(12) United States Patent
Bischoff et al.

(10) Patent No.: US 7,598,099 B2
(45) Date of Patent: Oct. 6, 2009

(54) METHOD OF CONTROLLING A FABRICATION PROCESS USING AN ISO-DENSE BIAS

(75) Inventors: Joerg Bischoff, Iimenau (DE); Heiko Weichert, Utzberg (DE)

(73) Assignee: Tokyo Electron Limited, Tokyo (JP)

( * ) Notice: Subject to any disclaimer, the term of this patent is extended or adjusted under 35 U.S.C. 154(b) by 110 days.

(21) Appl. No.: 11/936,769

(22) Filed: Nov. 7, 2007

(65) Prior Publication Data

US 2009/0118857 A1    May 7, 2009

(51) Int. Cl.
*H01L 21/66* (2006.01)

(52) U.S. Cl. .............................. 438/16; 438/14; 438/17; 438/18; 438/32; 438/400; 438/455; 257/E21.525; 257/E21.529; 257/E21.53

(58) Field of Classification Search .............. 438/5, 438/6, 7, 10, 11, 14, 16, 17, 18, 32, 400, 438/455; 257/E21.525, E21.529, E21.53
See application file for complete search history.

(56) References Cited

U.S. PATENT DOCUMENTS

| | | | |
|---|---|---|---|
| 6,479,309 B1 * | 11/2002 | Wright | 438/16 |
| 6,785,638 B2 | 8/2004 | Niu et al. | |
| 6,891,626 B2 | 5/2005 | Niu et al. | |
| 6,943,900 B2 | 9/2005 | Niu et al. | |
| 7,099,081 B2 * | 8/2006 | Norton et al. | 359/497 |
| 7,209,798 B2 | 4/2007 | Yamashita et al. | |
| 2004/0267397 A1 | 12/2004 | Doddi et al. | |
| 2006/0064193 A1 | 3/2006 | Yamashita et al. | |
| 2008/0002213 A1 * | 1/2008 | Weiss | 356/620 |
| 2008/0183412 A1 * | 7/2008 | Funk et al. | 702/97 |

OTHER PUBLICATIONS

U.S. Appl. No. 11/408,744, Nolet et al., "Optimized characterization of water structures for optical metrology".
U.S. Appl. No. 11/848,214, Liu et al., "Automated process control using parameters determined with approximation and fine diffraction models".

* cited by examiner

*Primary Examiner*—Thanh V Pham
(74) *Attorney, Agent, or Firm*—Manuel B. Madriaga

(57) ABSTRACT

Embodiments of controlling a fabrication process using an iso-dense bias are generally described herein. Other embodiments may be described and claimed.

9 Claims, 8 Drawing Sheets

| | Dose (mJ/cm^2) | 20 | 21.25 | 22.5 | 23.75 | 25 |
|---|---|---|---|---|---|---|
| | $\sigma_i$ | | | | | |
| ICD | 0.6 | 99.8 | 94.1 | 88.9 | 84 | 79.4 |
| | 0.645 | 96.1 | 90.3 | 85 | 80.1 | 75.5 |
| | 0.69 | 91.6 | 85.8 | 80.3 | 75.4 | 70.7 |
| | 0.735 | 85.3 | 79.5 | 74.1 | 68.9 | 20.9 |
| | 0.78 | 79.3 | 73.2 | 25 | 6.3 | 0 |
| | | | | | | |
| DCD | 0.6 | 89.3 | 80 | 71.2 | 62.7 | 54.2 |
| | 0.645 | 88.4 | 79.7 | 71.6 | 63.8 | 56 |
| | 0.69 | 88 | 79.7 | 72 | 64.6 | 57.2 |
| | 0.735 | 87.9 | 79.9 | 72.5 | 65.4 | 58.3 |
| | 0.78 | 88 | 80.1 | 72.8 | 65.9 | 59.1 |
| | | | | | | |
| $\Delta_{IB}$ | 0.6 | 10.5 | 14.1 | 17.7 | 21.3 | 25.2 |
| | 0.645 | 7.7 | 10.6 | 13.4 | 16.3 | 19.5 |
| | 0.69 | 3.6 | 6.1 | 8.3 | 10.8 | 13.5 |
| | 0.735 | -2.6 | -0.4 | 1.6 | 3.5 | -37.4 |
| | 0.78 | -8.7 | -6.9 | -47.8 | -59.6 | -59.1 |

FIG. 9

| | Dose (mJ/cm^2) | 20 | 21.25 | 22.5 | 23.75 | 25 |
|---|---|---|---|---|---|---|
| | $\sigma_i$ | | | | | |
| ICD | 0.6 | 116.3 | 110.1 | 104.6 | 99.5 | 95 |
| | 0.645 | 110.4 | 104.2 | 98.5 | 93.4 | 88.8 |
| | 0.69 | 107.1 | 100.7 | 95 | 89.7 | 84.8 |
| | 0.735 | 104.5 | 98.1 | 92.4 | 87 | 81.8 |
| | 0.78 | 104.5 | 98 | 92.1 | 86.7 | 81.4 |
| | | | | | | |
| DCD | 0.6 | 88.4 | 77.4 | 67 | 56.7 | 46.3 |
| | 0.645 | 99.3 | 88.3 | 78.1 | 68.7 | 59.6 |
| | 0.69 | 109 | 98.2 | 87.9 | 78.5 | 70.6 |
| | 0.735 | 116.9 | 105.7 | 96.6 | 87.5 | 79 |
| | 0.78 | 124.2 | 113.2 | 103.4 | 94.4 | 87.2 |
| | | | | | | |
| $\Delta_{IB}$ | 0.6 | 27.9 | 32.7 | 37.6 | 42.8 | 48.7 |
| | 0.645 | 11.1 | 15.9 | 20.4 | 24.7 | 29.2 |
| | 0.69 | -1.9 | 2.5 | 7.1 | 11.2 | 14.2 |
| | 0.735 | -12.4 | -7.6 | -4.2 | -0.5 | 2.8 |
| | 0.78 | -19.7 | -15.2 | -11.3 | -7.7 | -5.8 |

FIG. 10

METHOD OF CONTROLLING A FABRICATION PROCESS USING AN ISO-DENSE BIAS

FIELD OF THE INVENTION

The field of invention relates generally to optical metrology and, more particularly, to the use of optical metrology to monitor one or more output parameters from an upstream process or processes and providing feedback to adjust the output parameters from the upstream process or processes.

BACKGROUND INFORMATION

Periodic gratings are typically used for process monitoring and control in the field of semiconductor manufacturing. The periodic gratings may be one or more lines fabricated in series on a workpiece. For example, one typical use of periodic gratings includes fabricating a periodic grating in proximity to the operating structure of a semiconducting chip. The periodic grating is then illuminated with an electromagnetic radiation by an optical metrology tool. The electromagnetic radiation that deflects off of the periodic grating are collected as a diffraction signal. The diffraction signal is then analyzed to determine whether the periodic grating, and by extension whether the operating structure of the semiconductor chip, has been fabricated according to specifications.

In one conventional system, the diffraction signal collected from illumination of the periodic grating (the measured diffraction signal) is compared to a library of simulated diffraction signals. Each simulated diffraction signal in the library is associated with a hypothetical profile. When a match is made between the measured diffraction signal and one of the simulated diffraction signals in the library, the hypothetical profile associated with the simulated diffraction signal is presumed to represent the actual profile of the periodic grating.

The actual profile of the periodic grating may represent a series of features with very tightly controlled parameters, or critical dimensions. The critical dimension may be a line width, a space width, or a contact length. The series of features may be tightly arranged in dense regions and loosely arranged in isolated regions. The combination of at least one dense region and at least one isolated region is a repeating structure. A diffraction signal measured from a feature in an isolated region may be very different from a diffraction signal measured from a similarly-sized feature in a dense region.

The diffraction signal measured from an isolated structure in an isolated region is used to determine an isolated structure critical dimension (ICD). The diffraction signal measured from a dense structure in a dense region is used to determine a dense structure critical dimension (DCD). The difference between the isolated structure critical dimension (ICD) and the dense structure critical dimension (DCD) is known as the iso-dense bias ($\Delta_{IB}$), $$\Delta_{IB} = ICD - DCD$$

The iso-dense bias is accounted for by the optical metrology tool so that similarly sized features may be measured consistently, independent of surrounding features. Currently, the iso-dense bias is determined by making at least one measurement of features in a dense region and a second measurement of features in an isolated region to find a difference between the isolated structure critical dimension (ICD) and the dense structure critical dimension (DCD). This requires consecutive measurements of at least one metrology grating target with isolated an line and one grating target with dense lines. The iso-dense bias is represented by the difference between these measurements. Calculating the iso-dense bias using this methodology requires multiple, time-consuming measurements by the optical metrology tool.

BRIEF DESCRIPTION OF THE DRAWINGS

The present invention is illustrated by way of example and not as a limitation in the figures of the accompanying drawings, in which

FIG. 9 is a table of measurement data of an isolated line-space profile and a dense line-space profile;

FIG. 10 is a table of measurement data of a hybrid grating profile;

DETAILED DESCRIPTION

Figure 1:
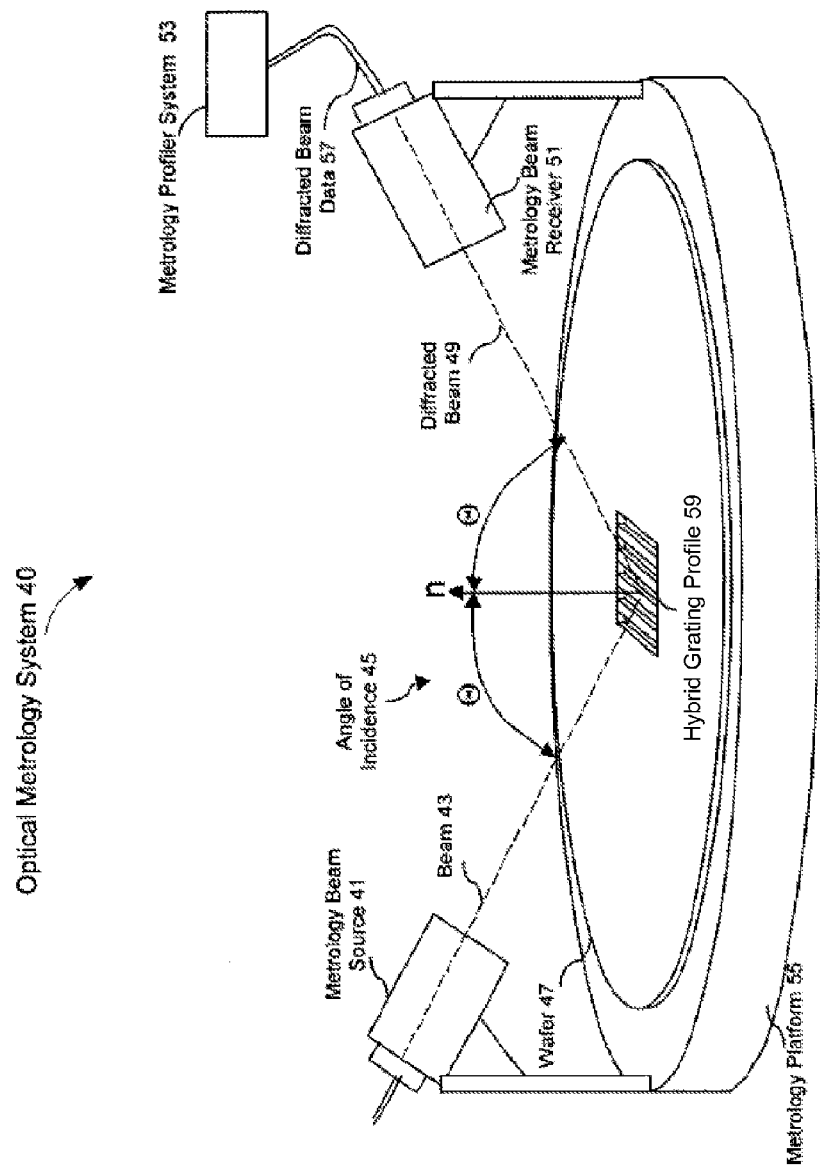
FIG. 1 is an illustration of the use of optical metrology to measure diffracted spectra from a grating layer.

A method of using optical metrology to monitor one or more output parameters from an upstream process or processes and providing feedback to adjust output parameters from the upstream process or processes is disclosed in various embodiments. However, one skilled in the relevant art will recognize that the various embodiments may be practiced without one or more of the specific details, or with other replacement and/or additional methods, materials, or components. In other instances, well-known structures, materials, or operations are not shown or described in detail to avoid obscuring aspects of various embodiments of the invention. Similarly, for purposes of explanation, specific numbers, materials, and configurations are set forth in order to provide a thorough understanding of the invention. Nevertheless, the invention may be practiced without specific details. Furthermore, it is understood that the various embodiments shown in the figures are illustrative representations and are not necessarily drawn to scale.

Reference throughout this specification to "one embodiment" or "an embodiment" means that a particular feature, structure, material, or characteristic described in connection with the embodiment is included in at least one embodiment of the invention, but do not denote that they are present in every embodiment. Thus, the appearances of the phrases "in one embodiment" or "in an embodiment" in various places throughout this specification are not necessarily referring to the same embodiment of the invention. Furthermore, the particular features, structures, materials, or characteristics may be combined in any suitable manner in one or more embodiments. Various additional layers and/or structures may be included and/or described features may be omitted in other embodiments.

Various operations will be described as multiple discrete operations in turn, in a manner that is most helpful in understanding the invention. However, the order of description should not be construed as to imply that these operations are necessarily order dependent. In particular, these operations need not be performed in the order of presentation. Operations described may be performed in a different order than the described embodiment. Various additional operations may be performed and/or described operations may be omitted in additional embodiments.

There is a general need to monitor one or more output parameters from an upstream process or processes and provide feedback to adjust process parameters and/or equipments settings of the upstream process or processes. An example of an output parameter that may be used for process monitoring is iso-dense bias. A change in iso-dense bias may be used to detect changes in output produced by an upstream process or by a series of upstream processes. One embodiment of a method of controlling a fabrication process using iso-dense bias comprises forming a grating layer on a workpiece using the fabrication process, providing the workpiece with the grating layer comprising a plurality of repeating profiles to a metrology tool, each repeating profile comprising a dense region and an isolated region, the dense region comprising a plurality of features including a comparison structure, the isolated region including an isolated structure, the plurality of features in the dense region and the isolated feature in the isolated region configured in a pattern such that an iso-dense bias between the isolated feature and the dense feature is within a range determined for the workpiece. The grating layer is exposed to electromagnetic energy and a diffraction signal is measured from the electromagnetic energy diffracted by the grating layer and an iso-dense bias is determined. The iso-dense bias is transmitted to a fabrication cluster wherein the fabrication cluster was used to create the grating layer on the workpiece, the fabrication cluster having a plurality of process parameters and equipment settings. One or more process parameters or equipment settings of the fabrication cluster are adjusted based at least on the iso-dense bias.

FIG. 1 is an illustration of the use of an optical metrology system to measure the diffracted spectra from a grating layer. The optical metrology system 40 consists of a metrology beam source 41 projecting a beam 43 at the hybrid grating profile 59 of a workpiece or wafer 47 mounted on a metrology platform 55. The beam 43 is projected at an incidence angle theta ($\theta$) towards the hybrid grating profile 59. The diffracted beam 49 is measured by a beam receiver 51. The diffracted beam data 57 is transmitted to a metrology profiler system 53. The metrology profiler system 53 compares measured diffracted beam data 57, or measured diffraction signal against a library of simulated diffracted beam data, or simulated diffraction signal representing varying combinations of profile parameters of the hybrid grating profile 59 and resolution.

The optical metrology system 40 is configured to determine one or more profile parameters of a hybrid grating profile 59 using any number of methods which provide a best matching simulated diffraction signal to a measured diffraction signal. These methods can include a library-based process, or a regression based process using simulated diffraction signals obtained by applying Maxwell's equations and using a numerical analysis technique to solve Maxwell's Equations, such as rigorous coupled wave analysis (RCWA) and machine learning systems. For a discussion, see U.S. Pat. No. 6,891,626, titled CACHING OF INTRA-LAYER CALCULATIONS FOR RAPID RIGOROUS COUPLED-WAVE ANALYSES, filed on Jan. 25, 2001, issued May 10, 2005, which is incorporated herein by reference in its entirety. The simulated diffraction signal may also be generated using a machine learning system (MLS) employing a machine learning algorithm, such as back-propagation, radial basis function, support vector, kernel regression, and the like. See, U.S. Patent Publication No. US 2004-0267397 A1, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety. See also, U.S. Pat. No. 6,943,900, titled GENERATION OF A LIBRARY OF PERIODIC GRATING DIFFRACTION SIGNALS, filed on Jul. 16, 2001, issued Sep. 13, 2005, which is incorporated herein by reference in its entirety; U.S. Pat. No. 6,785,638, titled METHOD AND SYSTEM OF DYNAMIC LEARNING THROUGH A REGRESSION-BASED LIBRARY GENERATION PROCESS, filed on Aug. 6, 2001, issued Aug. 31, 2004, which is incorporated herein by reference in its entirety; and U.S. Pat. No. 6,891,626, titled CACHING OF INTRA-LAYER CALCULATIONS FOR RAPID RIGROUS COUPLED-WAVE ANALYSES, filed on Jan. 25, 2001, issued May 10, 2005, which is incorporated herein by reference in its entirety.

The library instance best matching the measured diffracted beam data 57 is selected. The profile and associated critical dimensions of the selected library instance correspond to the cross-sectional profile and critical dimensions of the features of the hybrid grating profile 59. The optical metrology system 40 may utilize a reflectometer, an ellipsometer, or other optical metrology device to measure the diffracted beam or spectrum.

Figure 2A:
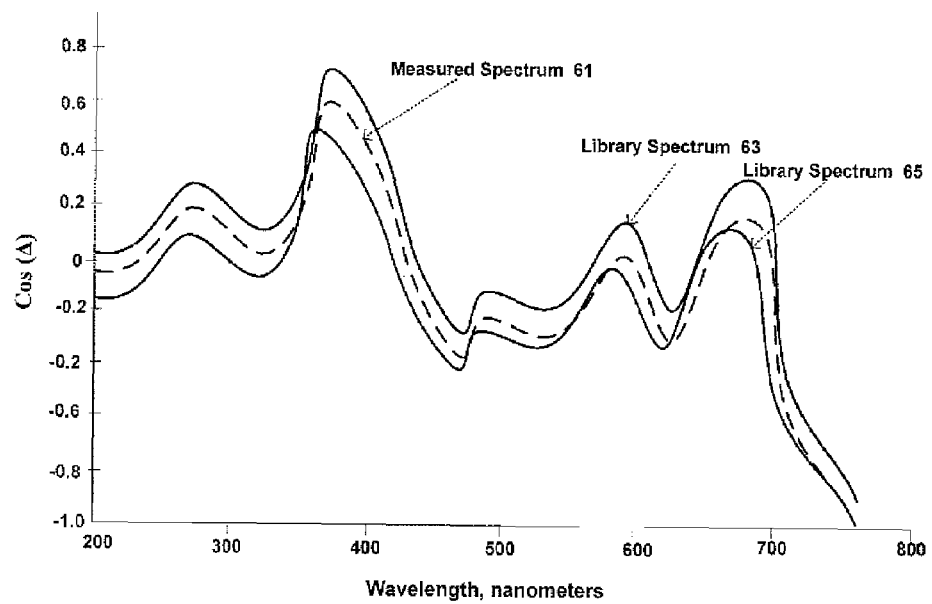
FIG. 2A illustrates a measured diffracted spectrum graph compared to diffracted spectra graphs of instances in a profile library.

FIG. 2A illustrates a measured diffracted spectrum graph compared to diffracted spectra graphs of instances in a profile library. The wavelength in nanometers (nm) is shown in the X-axis and cosine delta ($\Delta$), an ellipsometric measurement of the diffracted spectrum, in the Y-axis. A profile library is created with ranges of CD's and other profile parameters of structures in a wafer. The number of instances of the profile library is a function of the combinations of the various CD's and other profile parameters at the specified resolution. For example, the range of the top CD for the dense lines and the isolated lines of the hybrid grating may vary from 40 to 80 nm and the specified resolution is 0.5 nm. In combination with the other profile parameters of the structure, one or more instances of the profile library are created starting at 40 nm top CD and for every, 0.5 nm increment thereafter until 80 nm. For example, instances of a profile library for trapezoidal profiles may have diffracted spectra and profile parameters including a top CD, a bottom CD, and height. In FIG. 2A, a first library spectrum 63 representing a set of the profile parameters at a given resolution and a second library spectrum 65 with a different set of profile parameters at the same resolution are illustrated. A measured diffracted spectrum 61 is in close proximity to library spectra 63 and 65. One aspect of the present invention is to determine the profile model of an optical digital profilometry model that corresponds to the measured diffracted spectrum 61 based on the measured diffracted spectrum 61 and on known values in the profile library.

Figure 2B:
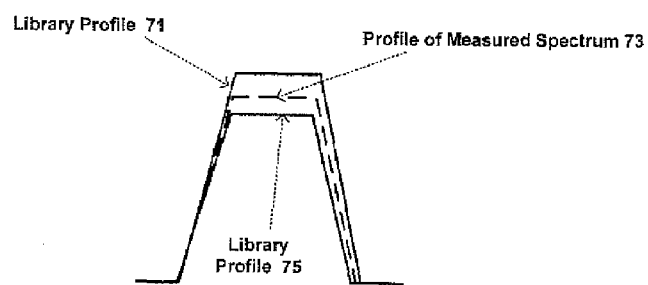
FIG. 2B illustrates a structure profile of a measured periodic structure compared to profiles of instances in a profile library.

FIG. 2B illustrates a structure profile of a measured periodic structure compared to profiles of instances in a profile library. A first library profile 71 of a trapezoidal structure is illustrated with a second library profile 75. A measured diffracted spectrum corresponds to a profile 73, shown as a dotted line, with profile parameters that are in close proximity to library profiles 71 and 75. As an example, assume that the first library profile 71 corresponds to the first library spectrum 63 and that the second library profile 75 corresponds to the second library spectrum 65. As depicted in FIG. 2A, neither library spectrum 63 or 65 exactly matches the measured diffracted spectrum 61. As such, in most conventional systems, based on a "best match" algorithm, either library spectrum 63 or 65 would be selected as the closest match. However, this results in a certain amount of error. For example, assume that the second library spectrum 65 is selected as a match for measured diffracted spectrum 61. In that case, the second library profile 75 is selected as representing the actual profile of the periodic grating.

However, as depicted in FIG. 2B, there is a difference/error between the second library profile 75 and the actual profile of the periodic grating (i.e., the profile 73). One solution may be to increase the resolution of the library so that there would be a library spectrum that more closely matches the measured spectrum. However, this increases the size of the library, which has the disadvantage of more time and computation to generate the library, to store the library, and to search the library.

Figure 3:
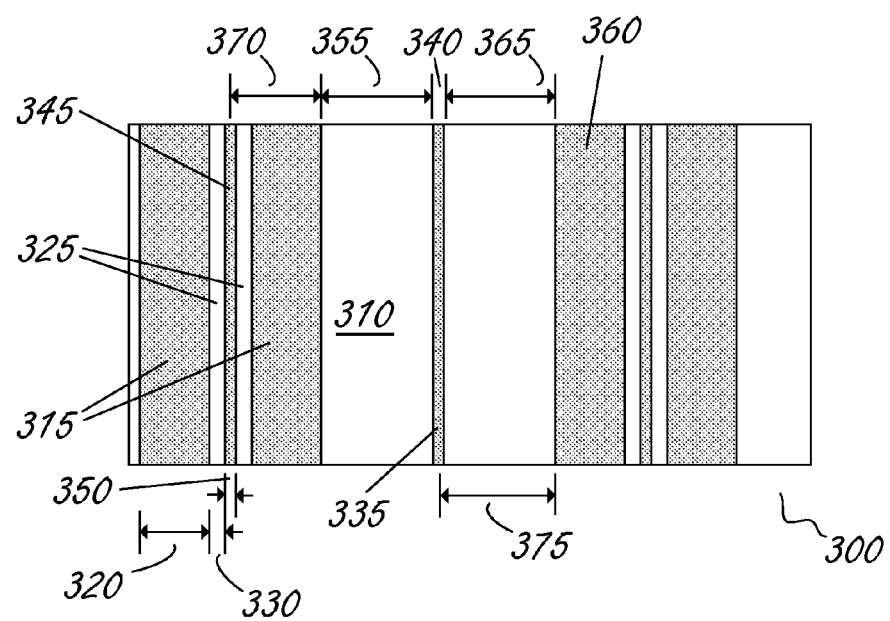
FIG. 3 is an illustration of a top view of one embodiment of a hybrid grating profile.

FIG. 3 is an illustration of a top view of one embodiment of repeating features formed as a hybrid grating profile 59 as part of the wafer 47 in FIG. 1. A first reference grating 300 is one embodiment of the hybrid grating profile 59 that is comprised of a series of dense features adjacent to an isolated line structure 335, separated by a large separation 310. In this embodiment, a combination of a plurality of dense features comprising a comparison line structure 345 and an isolated feature comprising at least one isolated line structure 335 creates a hybrid grating profile 59.

In one embodiment, a dense structure 315 is separated from a comparison line structure 345 by a narrow space 325 to form a dense feature. The narrow space 325 may have a narrow space width 330 that is equal to or up to two times as large as a comparison line structure width 350, though the embodiment is not so limited. In one embodiment, the comparison line structure width 350 ranges approximately between 15 and 200 nm. In another embodiment, the comparison structure width ranges approximately between 50 and 100 nm. For example, the comparison line structure width 350 may range approximately between 60 and 90 nm and the narrow space width may range approximately between 90 and 120 nm.

A dense structure width 320 may be approximately equal to or larger than the comparison line structure width 350. In one embodiment, the dense structure width 320 may range approximately between 15 and 1000 nm. In another embodiment, the dense structure width 320 may range approximately between 200 and 700 nm. For example, the dense structure width 320 may range approximately between 400 and 500 nm.

The comparison line structure width 350 may also be approximately equal to or narrower than an isolated line structure width 340. For example, the isolated line structure width 340 may range approximately between 50 and 400 nm. In another example, the isolated line structure width 340 may range approximately between 100 and 200 nm. Also, a distance between the isolated line structure 335 and the comparison line structure 345 should exceed a coherence length of an optical stepper or scanner, which is defined by an illumination wavelength, a numerical aperture and a coherence parameter ($\sigma_i$).

The comparison structure may be surrounded by a plurality of dense structures 315, as shown in FIG. 3. However, the order and shape of dense structures 315, comparison line structures 345, and narrow spaces 325 may differ from the embodiment shown in FIG. 3. Critical dimensions of features may be in the form of structures, they may be in the form of spaces between the structures, or they may be some combination of features thereof. As an example, the comparison line structure width 350, the isolated line structure width 340, the narrow space width 330, and the dense structure width 320 may each be critical dimensions.

The isolated line structure 335 may be a line, a rectangle, or some other geometric shape or some variant thereof, though the embodiment is not so limited. The separation 310 may have a separation width 355 that is two to four times as large as an isolated line structure width 340. The dense structure 315, the comparison line structure 345, and the isolated line structure 335 may be separated from a neighboring structure 360 by a gap width 365 wherein the gap width 365 is equal to or greater than the separation width 355. In one embodiment, it is preferred to provide a separation width 355 that is equal to or approximately equal to the gap width 365.

In one embodiment, to avoid optical proximity effects, a dense feature offset 370 measured from a midpoint of the comparison line structure 345 to a distal edge of the dense structure 315, and an isolated feature offset 375 measured from a midpoint of the isolated line structure 335 to a neighboring structure 360 as shown in FIG. 3 are each greater than a coherence diameter of a lithography system used to define a plurality of structures comprising the comparison line structure 345 and the dense structure 315. A range determined for the workpiece, in one embodiment, may mean that the dense feature offset 370 measured from a midpoint of the comparison line structure 345 to a distal edge of the dense structure 315, and the isolated feature offset 375 measured from a midpoint of the isolated line structure 335 to a neighboring structure 360 as shown in FIG. 3 are each equal to or up to two times greater than the coherence diameter of the lithography system used to define a plurality of structures comprising the comparison line structure 345 and the dense structure 315. In another embodiment, the dense feature offset 370 and the isolated feature offset 375 are each equal to or up to 5 times greater than the coherence diameter of the lithography system used to define a plurality of structures comprising the comparison line structure 345 and the dense structure 315.

The coherence diameter ($d_{wafer}$) is defined according to basic principles of optical lithography imaging, as the wavelength ($\lambda$) of an illumination source divided by a coherence parameter ($\sigma$) and a wafer side numerical aperture of the scanner lens ($NA_{wafer}$), expressed as:

$$d_{wafer} = \frac{\lambda}{\sigma \cdot NA_{wafer}}$$

Wherein the coherence parameter ($\sigma$) is a ratio of the numerical aperture of the illumination source $NA_{illu}$ and the mask side numerical aperture of the scanner lens $NA_{mask}$, expressed as:

$$\sigma = \frac{NA_{illu}}{NA_{mask}}$$

Design of a hybrid grating profile 59, illustrated in FIG. 3 through FIG. 8 should be performed to avoid optical proximity effects, as discussed supra.

A mask design of the hybrid grating profile 59 is determined by printing conditions and other processing conditions. For example, a positive resist process would require a positive mask whereas a negative resist process would require a negative mask. In order to print a mask pattern of FIG. 4 onto a wafer, a negative resist process would require a tone reversal. In another embodiment, a pattern is printed that is the reverse of FIG. 4, i.e., lines become spaces and vice versa. In this case, the mask has to be reversed correspondingly. The feature sizes, including any critical dimensions on the mask are defined by the targeted feature sizes on the wafer and by the reduction ratio (ex. 4:1 for DUV Lithography). Resolution enhancement techniques such as phase shifting masks (PSM), Optical Proximity Correction (OPC) features and Double Patterning Lithography (DPL) may be applied for the design of the hybrid mask to insure the correct printing of critical features.

Figure 4:
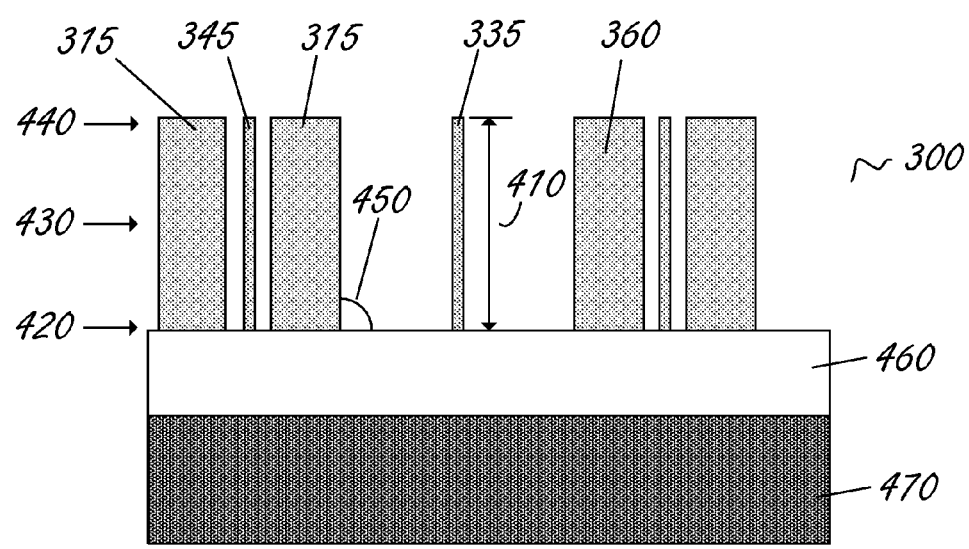
FIG. 4 is an illustration of a side view of the hybrid grating profile of FIG. 3.

FIG. 4 is an illustration of a side view of the hybrid grating profile 59 of FIG. 3. The first reference grating 300 may comprise an isolated line structure 335, a comparison line structure 345, a dense structure 315, and a base layer 460 on a substrate 470. The substrate 470 may comprise silicon, strained silicon, gallium arsenide, gallium nitride, silicon germanium, silicon carbide, carbide, diamond, and/or other materials such as a buried insulating layer. The base layer 460 may be a doped or undoped epitaxial layer, a bottom anti-reflective coating layer, a resist layer, or a hard mask layer comprising silicon oxide, silicon nitride or silicon oxynitride formed on the substrate 470 using methods known to one skilled in the art. The base layer 460 may be comprised of a single material or the base layer 460 may be a plurality of layered and unpatterned or patterned films. The plurality of dense structures 315, at least one comparison line structure 345, and at least one isolated line structure 335 may be formed on the base layer 460 or, alternatively, on the substrate 470 from one or more resist, anti-reflective coating, silicon nitride, or silicon oxide layers using methods known to one skilled in the art.

Each structure width and height, for example an isolated structure height 410, including the dense structure 315, isolated line structure 335, comparison line structure 345 and the separation 310 and narrow space 325 may each be characterized as critical dimensions. The location of the critical dimension of a structure may be at a bottom location 420 proximal to the base layer 460, a top location 440 distal from the base layer 460, or at some intermediate location 430 between the bottom location 420 and the top location 440. A sidewall angle 450 of each structure may also be a critical dimension. An iso-dense bias is derived as a difference between a determined critical dimension for the isolated line structure 335 and a determined critical dimension for the comparison line structure 345. Determining a critical dimension is the result of a determination process using regression, libraries, and/or machine learning systems and the measured diffraction signal or diffracted spectrum. In one embodiment, the iso-dense bias is the difference between the isolated line structure width 340 measured at the top location 440 and the comparison line structure width 350 measured at the top location 440 from a two dimensional perspective. In another embodiment, the iso-dense bias is the difference between the isolated line structure width 340 at the intermediate location 430 and the comparison line structure width 350 at the intermediate location 430 in a three dimensional manner, though the embodiment is not so limited.

Figure 5:
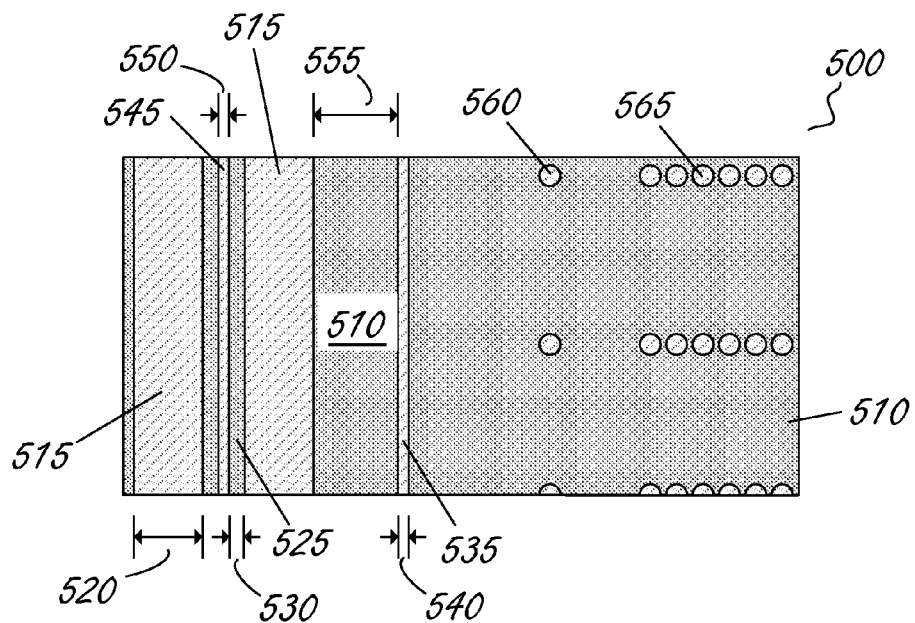
FIG. 5 is an illustration of a top view of an embodiment of an array of embedded elements formed as a hybrid grating profile as part of the wafer.

FIG. 5 is an illustration of a top view of an embodiment of an array of embedded elements formed as a hybrid grating profile 59 as part of the wafer 47 in FIG. 1. The second reference grating 500 is another embodiment of the hybrid grating profile 59 that is comprised of a series of dense elements adjacent to an isolated element 535, separated by a large form 510. In this embodiment, a dense element 515 is separated from a comparison element 545 by a narrow form 525 to create a dense feature. The narrow form 525 may have a narrow form width 530 that is approximately two times as large as a comparison structure width 550, though the narrow form 525 may be smaller than the comparison element width 550. A dense form width 520 may be approximately equal to or larger than the comparison element width 550. The comparison element width 550 may be approximately equal to an isolated element width 540. The comparison element width 550 and the isolated element width 540 may be critical dimensions. In another embodiment, the comparison element width 550 is within 20%, smaller or larger, of the isolated element width 540. The comparison element width 550 may also be a critical dimension. The comparison structure may be surrounded by a plurality of dense elements 515, as shown in FIG. 3. However, the order and shape of dense elements 515, comparison elements 545, and narrow forms 525 may differ from the embodiment shown in FIG. 3.

In an alternate embodiment, an isolated element may be a circular isolated element 560 and a comparison element may be a circular comparison element 565. However, the shape of the isolated element and the comparison element may be another geometric shape or some variant thereof.

Figure 6:
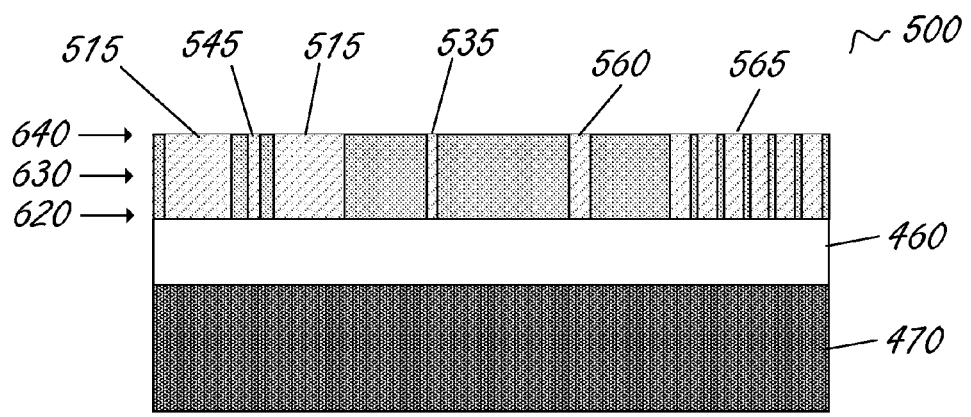
FIG. 6 is an illustration of a side view of the hybrid grating profile of FIG. 5.

FIG. 6 is an illustration of a side view of the hybrid grating profile of FIG. 5. The first reference grating 500 may comprise an isolated element 535, a comparison element 545, a dense element 515, and a base layer 460 on a substrate 470. The substrate 470 may comprise silicon, strained silicon, gallium arsenide, gallium nitride, silicon germanium, silicon carbide, carbide, diamond, and/or other materials such as a buried insulating layer. The base layer 460 may be a doped or undoped epitaxial layer, a bottom anti-reflective coating layer, a resist layer, or a hard mask layer comprising silicon oxide, silicon nitride or silicon oxynitride formed on the substrate 470 using methods known to one skilled in the art. The plurality of dense elements 515, at least one comparison element 545, and at least one isolated element 535 may be formed on the base layer 460 or, alternatively, on the substrate 470 from one or more resist, anti-reflective coating, silicon nitride, or silicon oxide layers using methods known to one skilled in the art.

Each element width and depth including the dense element 515, isolated element 535, comparison element 545 and the large form 510 and narrow form 525 may each be characterized as critical dimensions. The location of the critical dimension of a structure may be at a bottom location 620 proximal to the base layer 460, a top location 640 distal from the base layer 460, or at some intermediate location 630 between the bottom location 620 and the top location 640. A sidewall angle of each structure may also be a critical dimension. An iso-dense bias is calculated as a difference between a determined critical dimension for the isolated element 535 and a determined critical dimension for the comparison element 545. In one embodiment, the iso-dense bias is the difference between the isolated element width 540 measured at the top location 640 and the comparison element width 550 measured at the top location 640 in a two dimensional manner. In another embodiment, the iso-dense bias is the difference between the isolated element width 540 at the intermediate location 630 and the comparison element width 550 at the intermediate location 630 in a three dimensional manner, though the embodiment is not so limited.

Figure 7:
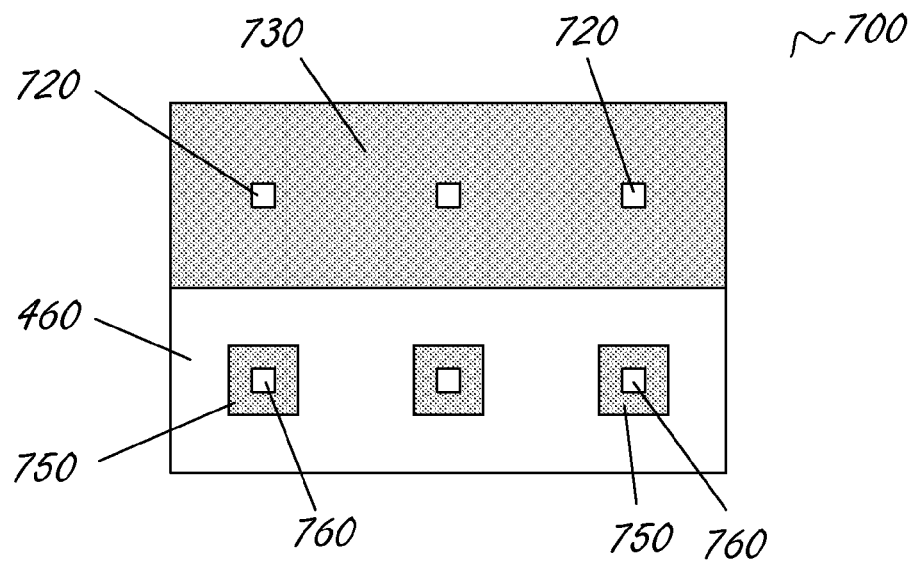
FIG. 7 is an illustration of another embodiment of a hybrid grating profile.

FIG. 7 is an illustration of another embodiment of a hybrid grating profile 59 as part of the wafer 47 in FIG. 1. A third reference grating 700 is one embodiment of the hybrid grating profile 59 that is comprised of a plurality of isolated vias 720 located proximate to a plurality of dense vias 760. In this embodiment, a combination of at least one dense via 760 and at least one isolated via 720 creates a hybrid grating profile 59.

In this embodiment, each isolated via 720 is square and approximately the same size and shape in this embodiment. In another embodiment, one or more isolated vias 720 may be unique in size and/or shape. Further in this embodiment, each isolated via 720 formed in an isolated via field 730 extends through the isolated via field 730 to a base layer 460. However, the isolated via 720 may be partially formed such that a bottom of the isolated via is situated along a depth of the isolated via field 730. The base layer 460 and/or the isolated via field 730 may be a doped or undoped epitaxial layer, a bottom anti-reflective coating layer, a resist layer, or a hard mask layer comprising silicon oxide, silicon nitride or silicon oxynitride formed on the substrate 470 using methods known to one skilled in the art.

A plurality of dense vias 760 are formed nearby in the same hybrid grating profile 59 on the base layer 460. In this embodiment, the dense vias 760 are formed in a dense via field 750 adjacent to a surrounding region of exposed base layer 460. In this embodiment, each dense via 760 is square and approximately the same size and shape in this embodiment. In another embodiment, one or more dense vias 760 may be unique in size and/or shape. For example, each dense via 760 may be circular, diamond, elliptical, hexagonal, or rectangularly shaped, though the embodiment is not so limited.

Figure 8:
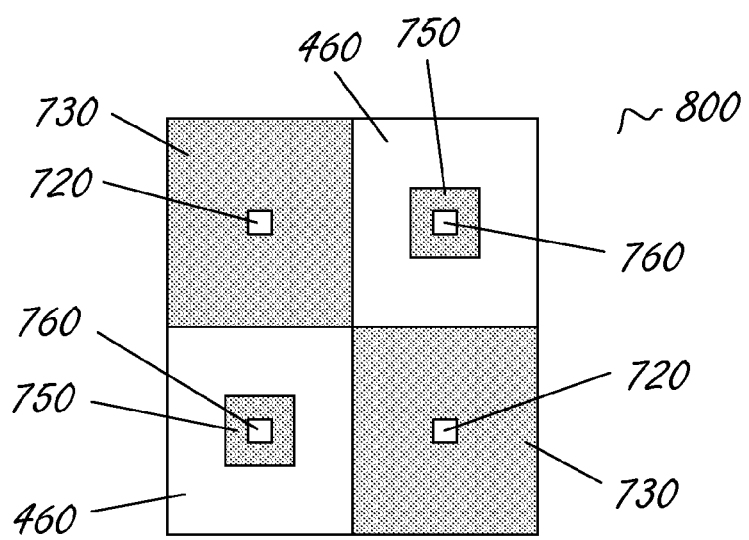
FIG. 8 is an illustration of a side view of the hybrid grating profile of FIG. 7.

FIG. 8 is an illustration of a further embodiment of a hybrid grating profile 59 as part of the wafer 47 in FIG. 1. A fourth reference grating 800 is another embodiment of the hybrid grating profile 59 that is comprised of a plurality of isolated vias 720 located proximate to a plurality of dense vias 760. In this embodiment, a plurality of dense vias 760 and a plurality of isolated vias 720 configured in a checkerboard design creates a hybrid grating profile 59. However, the plurality of dense vias 760 and the plurality of isolated vias 720 may be alternatively oriented in other patterns with a series of dense vias 760 configured adjacent to a plurality of isolated vias.

FIG. 9 is a table of lithography simulation data of an isolated line-space profile and a dense line-space profile. The measurement data in FIG. 9 was compiled by measuring an isolated critical dimension (ICD) separate from a dense critical dimension (DCD) measurement to derive an iso dense bias ($\Delta_{IB}$) where $\Delta_{IB}$=ICD−DCD. A two measurement process is performed according to prior art methods. Each $\Delta_{IB}$ value in FIG. 9 is a result of two separate measurements, a first measurement for the ICD and a second measurement for the DCD. In the table of FIG. 9, a dose of electromagnetic energy measured in milli-Joules per square centimeter (mJ/cm^2) is applied in a range from 20 to 25 mJ/cm^2 in increments of 1.25 mJ/cm^2 and a coherence parameter for annular illumination schema ($\sigma_i$), an optical parameter expressing a ratio of numerical aperture values, is varied from 0.6 to 0.78 in increments of 0.045 to form a matrix of measurement data and derived $\Delta_{IB}$. In this embodiment, a depth of focus of the optical metrology system 40 was set at zero, meaning that the focus plane was established at the top location 440 of the isolated line structure 335 and the comparison line structure of FIG. 3.

A well designed mask results in a good correlation between real iso-dense bias measured at isolated and dense grating patterns separately (see FIG. 9) and the iso-dense bias printed with the hybrid mask (see FIG. 10).

As an example, for the lithography simulation data in FIG. 9, it may be desirable to establish a minimal iso-dense bias between the ICD and the DCD. In that case, the minimal iso dense bias would be at a dose of 21.25 mJ/cm^2 at a $\sigma_i$ of 0.735.

FIG. 10 is a table of lithography simulation data of a line-space hybrid grating profile 59, such as the first reference grating 300 of FIG. 3. In this case, the measurement data in FIG. 10 was compiled by a single measurement of a hybrid grating profile 59 to derive an iso dense bias ($\Delta_{IB}$) where $\Delta_{IB}$=ICD−DCD. Each $\Delta_{IB}$ value in FIG. 9 is a result of a single measurement that is capable of deriving a first measurement for the ICD and a second measurement for the DCD. In the table of FIG. 10, a dose measured in milli-Joules per square centimeter (mJ/cm^2) is applied in a range from 20 to 25 mJ/cm^2 in increments of 1.25 mJ/cm^2 and a coherence parameter ($\sigma_i$) is varied from 0.6 to 0.78 in increments of 0.045 to form a matrix of measurement data and derived $\Delta_{IB}$. In this embodiment, a depth of focus of the optical metrology system 40 was set at zero, meaning that the focus plane was established at the top location 440 of the isolated line structure 335 and the comparison line structure of FIG. 3.

As an example, for the simulation data in FIG. 10, it may be desirable to establish a minimal iso dense bias between the ICD and the DCD. In that case, the minimal iso dense bias would be at a dose of 21.25 mJ/cm^2 at a $\sigma_i$ of 0.735. Alternatively, it may be desirable to monitor the iso dense bias, for example, by establishing an expected value for an iso dense bias, then monitoring a deviation from the expected value for subsequent hybrid grating profiles 59 measured by the optical metrology system 40. Subsequent wafers 47 with hybrid grating profiles 59 that have a deviation from an expected value that is equal to or greater than an established value may be flagged as non-conforming. As a result, a process may be monitored using a single measurement that takes into account a plurality of critical dimensions of a grating profile.

Figure 11:
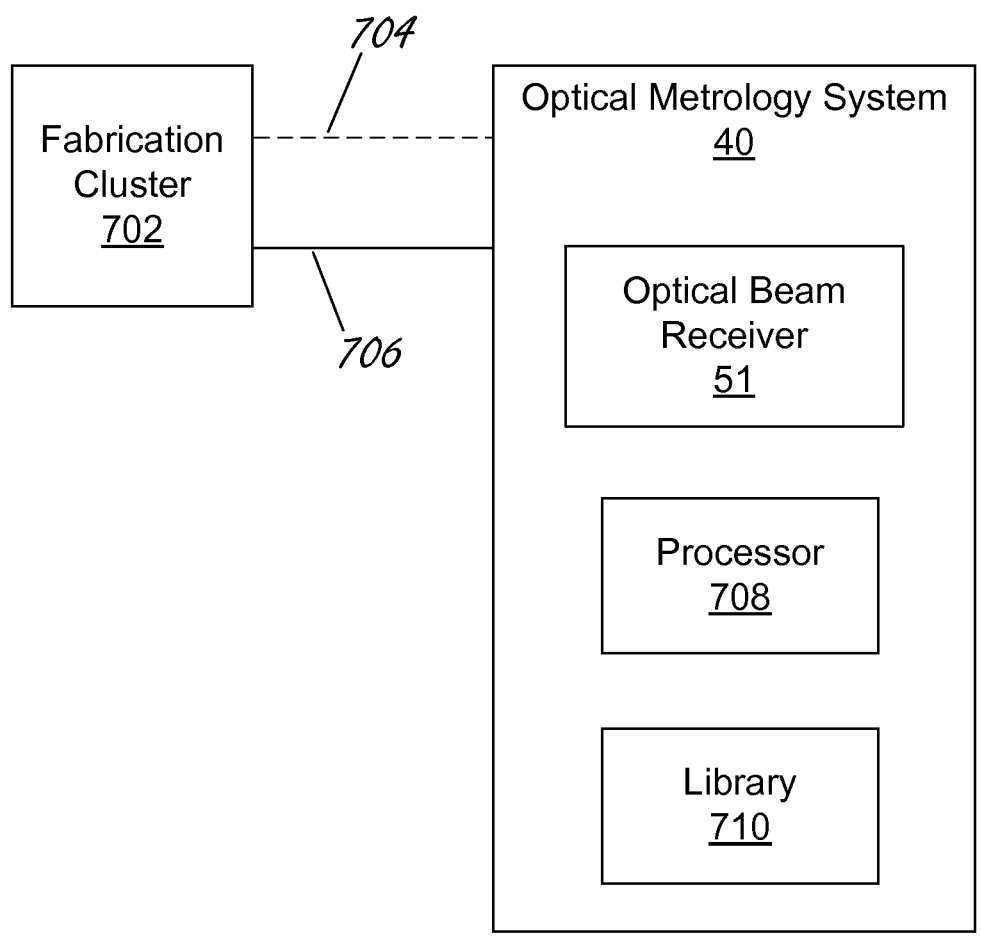
FIG. 11 is an exemplary block diagram of an optical metrology system coupled to a fabrication cluster.

FIG. 11 is an exemplary block diagram of an optical metrology system 40 coupled to a fabrication cluster 702 configured to provide a fabrication process. In one exemplary embodiment, optical metrology system 40 may include a library 710 with a plurality of simulated difference diffraction signals and a plurality of profile parameters associated with the plurality of simulated difference diffraction signals. Metrology processor 708 can calculate a simulated approximation diffraction signal and can compare a measured diffraction signal from a structure fabricated in fabrication cluster 702, adjusted by subtracting the simulated approximation diffraction signal, to the plurality of simulated difference diffraction signals in the library. Fabrication cluster 702 is configured to perform a fabrication process to fabricate one or more elements of a structure on a wafer. In one embodiment, the fabrication process is a lithography exposure process. In another embodiment, the fabrication process is a lithography develop process. Other examples of fabrication processes include processes used to fabricate semiconductor devices such as dry etch, chemical mechanical polishing, wet etch, chemical vapor deposition, physical vapor deposition, implantation, atomic layer deposition, and coating processes, though the embodiment is not so limited.

When a matching simulated difference diffraction signal is found, the profile parameters associated with the matching simulated difference diffraction signal in the library are assumed to correspond to the profile parameters of the actual structure measured by the optical beam receiver 51. A wireless communications link 704 may be provided to allow the optical metrology system 40 to communicate with the fabrication cluster 702.

The wireless communication link 704 may be in accordance with specific communication standards, such as the Institute of Electrical and Electronics Engineers (IEEE) standards including IEEE 802.11(a), 802.11(b), 802.11(g), and/or 802.11(n) standards and/or proposed specifications for wireless local area networks, although the scope of the invention is not limited in this respect as they may also be suitable to transmit and/or receive communications in accordance with other techniques and standards. For more information with respect to the IEEE 802.11, please refer to "IEEE Standards for Information Technology—Telecommunications and Information Exchange Between Systems"—Local Area Networks—Specific Requirements—Part 11 "Wireless LAN Medium Access Control (MAC) and Physical Layer (PHY), ISO/IEC 8802-11: 1999" and related amendments/versions.

Alternatively, or in combination with the wireless communications link, a wired communications link 706 may be provided to allow the optical metrology system 40 to communication with the fabrication cluster 702. The optical metrology system 40 can transmit digital data to the fabrication cluster 702 via wired communications link 706. The wired communications link 706 may be a physical medium such as an AC power line, telephone line or other electrical wire, a cable, a copper line, or the like. In one embodiment, the wired communications link 706 may be in accordance with specific communications standards, such as can communicate using one of many communication protocols, including Asynchronous Transfer Mode (ATM), IEEE 802.3 or 802.1, or a collection of standards defining a physical layer and a media access control sublayer of a data link layer of wired Ethernet.

Figure 12:
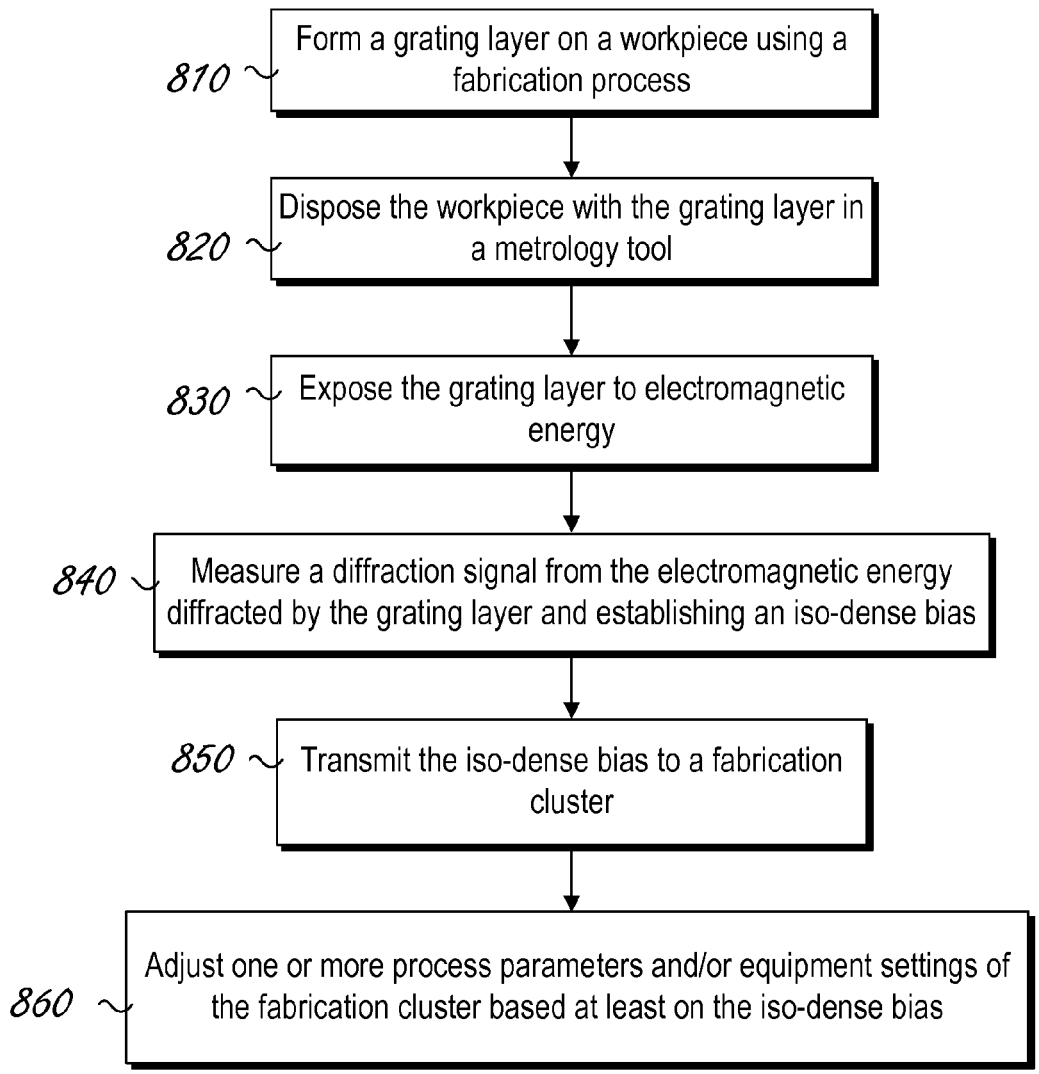
FIG. 12 is a flowchart describing one embodiment of a method of using optical metrology to monitor one or more output parameters from an upstream process or processes and providing feedback to adjust the output parameters from the upstream process or processes.

FIG. 12 is a flowchart describing one embodiment of a method of using an optical metrology system 40 to monitor one or more output parameters using a hybrid grating profile 59, as illustrated in FIG. 1 through FIG. 10, from the fabrication cluster 702 and providing feedback to adjust the output parameters from the fabrication cluster 702. The process may be initiated (element 810) by forming a grating layer or hybrid grating profile 59 comprising a plurality of repeating profiles on a workpiece 47 using a fabrication cluster 702, each repeating profile comprising a dense region and an isolated region, the dense region including a plurality of features including a comparison line structure 345, the isolated region including an isolated line structure 335. Also, each repeating profile is configured in a pattern so that the iso dense bias is within a range determined for the workpiece. The range for the iso dense bias may be established in part by the design of the hybrid grating profile 59, for example, by establishing a comparison line structure width 350 and an isolated line structure width 340 according to desired values and/or by modifying one or more measurement parameters of the optical metrology system 40 such as the dose, depth of field, or coherence parameter. The fabrication cluster 702 may be a single process tool or a plurality of process tools. For example, a fabrication cluster 702 may be a single dry etch system as known to one having skill in the art of semiconductor manufacturing. Alternatively, the fabrication cluster 702 may be a plurality of process tools, such as a lithography scanner combined with a lithography coater/developer.

The workpiece 47 with the grating layer is disposed in an optical metrology system 40 in element 820 and the grating layer on the workpiece 47 is exposed to electromagnetic energy in element 830. The electromagnetic energy may be provided by a spectroscopic source typically employed on a scatterometry type optical metrology system 40. One example of an optical metrology system 40 is an ellipsometry-based optical measurement and characterization system. In another embodiment, the optical metrology system 40 is a reflectometer or other optical metrology device to measure the diffracted beam or spectrum. In one embodiment, the beam 43 may impinge the hybrid grating profile 59 in a spot size measuring approximately between 20 and 200 microns. In another embodiment, the beam 43 may impinge the hybrid grating profile 59 in a spot size measuring approximately between 25 and 45 microns. The shape of the spot may be circular, elliptical, square, or rectangular, though the embodiment is not so limited.

A diffraction signal is measured from the electromagnetic energy diffracted by the grating layer and an iso-dense bias is determined in element 840. In element 850, the iso-dense bias and the second iso-dense bias are transmitted to the fabrication cluster using the wireless communication link 704 and/or the wired communications link 706. One or more process parameters and/or equipment settings are adjusted based at least on the iso-dense bias in element 860.

A plurality of embodiments of method of controlling a fabrication process using an iso-dense bias have been described. The foregoing description of the embodiments of the invention has been presented for the purposes of illustration and description. It is not intended to be exhaustive or to limit the invention to the precise forms disclosed. This description and the claims following include terms, such as left, right, top, bottom, over, under, upper, lower, first, second, etc. that are used for descriptive purposes only and are not to be construed as limiting. For example, terms designating relative vertical position refer to a situation where a device side (or active surface) of a workpiece 47 or integrated circuit is the "top" surface of that workpiece 47; the workpiece 47 may actually be in any orientation so that a "top" side of a workpiece 47 may be lower than the "bottom" side in a standard terrestrial frame of reference and still fall within the meaning of the term "top." The term "on" as used herein (including in the claims) does not indicate that a first layer "on" a second layer is directly on and in immediate contact with the second layer unless such is specifically stated; there may be a third layer or other structure between the first layer and the second layer on the first layer. The embodiments of a device or article described herein can be manufactured, used, or shipped in a number of positions and orientations.

Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. A method of controlling a fabrication process using iso dense bias, the method comprising:

defining a grating layer, the grating layer comprising a dense area with a plurality of dense features and an isolated area with at least one isolated feature;

forming the grating layer on a first substrate using a fabrication cluster;

providing the grating layer on the first substrate to a metrology tool;

exposing the grating layer to electromagnetic energy;

measuring a first diffraction signal from the electromagnetic energy diffracted by the grating layer and establishing a first iso-dense bias;

forming the grating layer on a second substrate using the fabrication cluster;

providing the grating layer on the second substrate to the metrology tool;

exposing the grating layer to electromagnetic energy;

measuring a second diffraction signal from the electromagnetic energy diffracted by the grating layer and establishing a second iso-dense bias;

transmitting the first iso-dense bias and the second iso-dense bias to the fabrication cluster wherein the fabrication cluster was used to create the grating layer on the first substrate and the second substrate, the fabrication cluster having process parameters and equipment settings; and adjusting one or more process parameters or equipment settings of the fabrication cluster based at least on the difference between the first iso-dense bias and the second iso-dense bias.

2. The method of claim 1, wherein the dense features and the isolated feature are formed in a layer on a substrate.

3. The method of claim 1, wherein the dense features and the isolated feature are formed from a layer on a substrate.

4. The method of claim 1, wherein a spot size for the electromagnetic energy is less than 55 microns.

5. The method of claim 1, wherein the metrology tool is a reflectometer or an ellipsometer.

6. The method of claim 1, wherein the electromagnetic energy is emitted from a monochromatic source.

7. The method of claim 1, wherein the electromagnetic energy is emitted from a spectroscopic source.

8. The method of claim 1, wherein the metrology tool is incorporated in the fabrication cluster.

9. The method of claim 1, wherein the fabrication cluster comprises a lithography exposure tool and a coater/developer system.

* * * * *